(12) United States Patent
Lana et al.

(10) Patent No.: US 9,658,177 B2
(45) Date of Patent: May 23, 2017

(54) APPARATUS, SYSTEM, AND METHOD FOR CATALYST PRESENCE DETECTION

(71) Applicant: Cummins Filtration IP, Inc., Columbus, IN (US)

(72) Inventors: Carlos Lana, Columbus, IN (US); Baohua Qi, Columbus, IN (US)

(73) Assignee: Cummins Filtration IP, Inc., Columbus, IN (US)

(*) Notice: Subject to any disclaimer, the term of this patent is extended or adjusted under 35 U.S.C. 154(b) by 0 days.

(21) Appl. No.: 15/019,661

(22) Filed: Feb. 9, 2016

(65) Prior Publication Data

US 2016/0161430 A1 Jun. 9, 2016

Related U.S. Application Data

(62) Division of application No. 12/965,682, filed on Dec. 10, 2010, now Pat. No. 9,303,545.

(60) Provisional application No. 61/285,390, filed on Dec. 10, 2009.

(51) Int. Cl.
| | | |
|---|---|---|
| *G01N 25/20* | (2006.01) | |
| *G01N 25/00* | (2006.01) | |
| *F01N 11/00* | (2006.01) | |
| *G01M 15/10* | (2006.01) | |

(52) U.S. Cl.
CPC .......... *G01N 25/00* (2013.01); *F01N 11/002* (2013.01); *G01M 15/102* (2013.01); *F01N 2550/24* (2013.01); *F01N 2900/1404* (2013.01); *Y02T 10/47* (2013.01)

(58) Field of Classification Search
None
See application file for complete search history.

(56) References Cited

U.S. PATENT DOCUMENTS

| | | |
|---|---|---|
| 4,969,328 A | 11/1990 | Kammel |
| 2002/0069643 A1 | 6/2002 | Yoshizawa et al. |
| 2004/0261374 A1 | 12/2004 | Bailey et al. |
| 2008/0083271 A1 | 4/2008 | He et al. |
| 2008/0314133 A1 | 12/2008 | Brinkmeier et al. |

OTHER PUBLICATIONS

The International Search Report and Written Opinion of the International Searching Authority, issued in PCT Application No. PCT/US2010/059938, dated Jul. 28, 2011.

*Primary Examiner* — Robert Xu
(74) *Attorney, Agent, or Firm* — Foley & Lardner LLP

(57) ABSTRACT

A system to detect the presence of a catalyst includes an exhaust gas tube, a first temperature sensing device, a second temperature sensing device, a flow rate measurement device, and a processing device. The first temperature sensing device measures a first temperature of exhaust gas upstream of the exhaust gas tube. The second temperature sensing device measures a second temperature of the exhaust gas downstream of the exhaust gas tube. The processing device estimates an expected time delay between the measured inlet and outlet exhaust gas temperatures corresponding to a system with a catalyst present. The processing device may also determine the presence of a catalyst by comparing the measured second temperature to the measured first temperature and comparing the measured second temperature to an estimated delayed first temperature associated with the expected time delay.

20 Claims, 6 Drawing Sheets

APPARATUS, SYSTEM, AND METHOD FOR CATALYST PRESENCE DETECTION

CROSS-REFERENCE TO RELATED APPLICATIONS

This patent application is a divisional of U.S. patent application Ser. No. 12/965,682, filed Dec. 10, 2010, which claims the benefit of U.S. Provisional Patent Application No. 61/285,390, filed Dec. 10, 2009, the contents of which are incorporated herein by reference.

FIELD

The present disclosure relates to exhaust aftertreatment systems for internal combustion engines, and more particularly to detecting the presence or absence of a catalyst of an exhaust aftertreatment system.

BACKGROUND

Regulations require that automobiles contain a catalyst detection system as part of the automobile's exhaust aftertreatment system to insure compliance with emission requirements. Catalysts in an exhaust aftertreatment system, such as an SCR catalyst, can be intentionally removed or not installed during assembly. Catalysts are key elements for the reduction of exhaust emissions and must be present for the exhaust aftertreatment system to work as intended. A missing catalyst may cause excessive nitrogen oxide (NOx) emission, excessive urea emission, potential NOx sensor damage, and/or other negative consequences.

Automatically detecting the presence of a catalyst in an exhaust aftertreatment system is often hindered due to the difficulty of distinguishing between common catalyst indicators and other problems within the exhaust aftertreatment system, such as a clogged urea doser and poor urea quality. When a diagnostic incorrectly identifies a missing catalyst that is in fact present, time and resources are unnecessarily spent to inspect the automobile only to find that the diagnostic has incorrectly indicated a missing catalyst.

Additionally, current methods of automatic catalyst detection may require that the automobile perform a cold soak prior to testing. Cold soaks require a long period of engine inactivity, which may take several hours and require extended engine-off time. This significantly decreases the in-use ratio of the automobile and the catalyst detection device.

Other known methods for detecting the presence of a catalyst using sensors can be ineffective due to the negative consequences associated with sensor uncertainties and miscalibration.

SUMMARY

From the foregoing discussion, it should be apparent that a need exists for an apparatus, system, and method that more effectively detect the presence of or damage to a catalyst. Beneficially, such an apparatus, system, and method would rely on exhaust temperature and flow sensing values, would not require a cold soak, and would be insensitive to both exhaust flow and temperature sensor errors.

The subject matter of the present disclosure has been developed in response to the present state of the art, and in particular, in response to the problems and needs in the art that have not yet been fully solved by currently available catalyst detection systems. Accordingly, the subject matter of the present disclosure has been developed to provide an apparatus, system, and method for detecting the presence of a catalyst in a catalyst housing that may overcome many or all of the above-discussed or other shortcomings in the art.

According to one embodiment, an apparatus to detect the present of a catalyst in a catalyst housing is provided with a plurality of modules configured to functionally execute the necessary steps of detecting a catalyst. Modules include a temperature module, a flow rate module, an expected time delay module, and a similarity module. In one embodiment, the temperature module detects a temperature of exhaust gas at an inlet of the catalyst housing and a temperature of exhaust gas at an outlet of the catalyst housing. In one embodiment, the flow rate module detects a flow rate of the exhaust gas through the catalyst housing. The expected time delay module estimates an expected time delay between the detected inlet and outlet exhaust gas temperatures in a normal system with a catalyst present based on the detected exhaust gas flow rate. Lastly, the similarity module determines a temperature similarity value based on the detected inlet and outlet exhaust gas temperatures and the delayed inlet exhaust gas temperature. In one embodiment, a catalyst is present if the determined temperature similarity value is above a first threshold and a catalyst is not present if the determined temperature similarity value is below a second threshold.

According to some implementations of the apparatus, the expected time delay module estimates the expected time delay via a Padé approximation of a pure time delay transfer function. The apparatus may also include a data buffer storing a plurality of measured time delays between the detected temperature of exhaust gas at the inlet of the catalyst housing and the detected temperature of exhaust gas at the outlet of the catalyst housing. The expected time delay module can estimate the expected time delay based on the plurality of measured time delays.

In certain implementations of the apparatus, the similarity module determines the temperature similarity value by comparing the detected temperature of exhaust gas at the outlet of the catalyst housing to: (1) the detected temperature of exhaust gas at the inlet of the catalyst housing; and (2) an estimated exhaust gas temperature at the outlet of the catalyst housing as if a catalyst were present in the catalyst housing, wherein the estimated exhaust gas temperature at the outlet of the catalyst housing comprises an estimated exhaust gas temperature at the inlet of the catalyst housing delayed by the expected time delay.

According to yet some implementations of the apparatus, the temperature similarity value is above the first threshold if the detected temperature of exhaust gas at the outlet of the catalyst housing is similar to the detected temperature of exhaust gas at the inlet of the catalyst housing, and the temperature similarity value is below the second threshold if the detected temperature of exhaust gas at the outlet of the catalyst housing is similar to the estimated exhaust gas temperature at the outlet of the catalyst housing as if a catalyst were present in the catalyst housing. The first and second threshold values can be the same.

In certain implementations of the apparatus, the temperature similarity value is defined as the parameter a that solves the optimization problem $$\hat{a} = \underset{a}{\operatorname{argmin}} \sum_k (T_o(k) - (aT_i(k-D) + (1-a)T_i(k)))^2.$$

In such implementations, â is the estimated similarity value, $T_o$ is the outlet temperature, $T_i$ is the inlet temperature, D is the expected delay, k is a discrete sample time, and the summation is over a predefined number of samples preceding the current time.

In yet certain implementations of the apparatus, the temperature similarity value is defined as the parameter a that solves the optimization problem $$\hat{a} = \operatorname*{argmin}_{a,b,g} \sum_k (T_o(k) - a(gT_i(k-D) + h) - (1-a)(gT_i(k) + h))^2.$$

In such implementations, â is an optimal or estimated similarity value, g is a inlet temperature sensor gain error correction, h is an inlet temperature sensor offset error correction, $T_o$ is the outlet temperature, $T_i$ is the inlet temperature, D is the expected delay, k is a discrete sample time, and the summation is over a predefined number of samples preceding the current time.

According to some implementations, the apparatus also includes an enablement module configured to enable the similarity module if at least one of a plurality of operating conditions are met and to disable the similarity module if none of the plurality of operating conditions are met. The plurality of operating conditions can include (1) the flow rate of exhaust gas falls within a first predetermined range; (2) both the detected temperature of exhaust gas at the inlet of the catalyst housing falls within a second predetermined range and the detected temperature of exhaust gas at the outlet of the catalyst housing falls within a third predetermined range; and (3) a change rate of the detected temperature of exhaust gas at the inlet of the catalyst housing falls within a fourth predetermined range.

In yet another embodiment, a system is presented to detect the presence of a catalyst. The system may be embodied to contain an exhaust gas tube, a first temperature sensing device, a second temperature sensing device, a flow rate measurement device, and a processing device. In one implementation, the exhaust gas tube is coupled with a diesel engine. Exhaust gas from the diesel engine is flowable through the exhaust gas tube. The first temperature sensing device is coupled to an upstream portion of the exhaust gas tube where it measures a first temperature of exhaust gas. The second temperature sensing device is coupled with a downstream portion of the exhaust gas tube where it measures a second temperature of the exhaust gas. The flow rate measurement device measures a flow rate of the exhaust gas. Additionally, the processing device estimates an expected time delay between the measured inlet and outlet exhaust gas temperatures corresponding to a system with a catalyst present. The processing device may also determine the presence of a catalyst by comparing the measured second temperature to the measured first temperature and comparing the measured second temperature to an estimated delayed first temperature associated with the expected time delay.

In some implementations of the system, the expected time delay is estimated based on the measured flow rate of the exhaust gas. According to certain implementations of the system, the processing device determines a catalyst is present if the measured second temperature and the estimated delayed first temperature are similar, and the processing device determines a catalyst is missing if the measured second temperature and the measured first temperature are similar. The expected time delay between the measured inlet and outlet exhaust gas temperatures can be defined as the expected time for a fluctuation in the inlet exhaust gas temperature to be observed by the second temperature sensing device.

According to another embodiment, a method is also presented for detecting the presence of a catalyst. The method substantially includes the steps necessary to carry out the functions presented above with respect to the operation of the described apparatus and system. In one implementation, the method includes measuring a flow rate of exhaust gas within an exhaust gas tube. The method may also include measuring an inlet temperature of the exhaust gas at an inlet of the exhaust gas tube. In one implementation, the method includes calculating an expected temperature time delay as a function of the measured flow rate.

The method may also include measuring an outlet temperature of the exhaust gas at an outlet of the exhaust gas tube and calculating a delayed inlet temperature based on the calculated expected temperature time delay and the inlet temperature. A first difference between the measured outlet temperature and the inlet temperature and a second difference between the measured outlet temperature and the delayed inlet temperature may also be calculated. In one embodiment, a catalyst is not present if the first difference is smaller than the second difference, and a catalyst is present if the second difference is smaller than the first difference.

In another embodiment, a second method is presented for detecting the presence of a catalyst. The method substantially includes the steps necessary to carry out the functions presented above with respect to the operation of the described apparatus and system. In one embodiment, the method includes detecting an inlet temperature of exhaust gas within an exhaust gas tube with a first temperature detection device. The method also includes measuring a flow rate of exhaust gas within the exhaust gas tube. Further, the method includes detecting an outlet temperature of the exhaust gas within the exhaust gas tube with a second temperature detection device.

In one implementation of the second method, a testing module is enabled and gain of the first temperature detection device and gain of the second temperature detection device are compared to calibrate the first temperature detection device and the second temperature detection device. An expected time delay between the measured inlet and outlet temperatures is determined and a first difference between the measured outlet temperature and the inlet temperature and a second difference between the measured outlet temperature and the delayed inlet temperature are calculated. An error message may be output if the first difference is smaller than the second difference.

According to another embodiment, a method for detecting the presence of a catalyst in an exhaust gas tube may include calculating a similarity value based on a catalyst housing outlet temperature, a catalyst housing inlet temperature, and a delayed catalyst housing inlet temperature, comparing the similarity value to a predetermined threshold, and determining if a catalyst is present or not present based on the comparison between the similarity value and the predetermined threshold. Calculating the similarity value may include solving an optimization problem. Additionally or alternatively, calculating the similarity value may include using a recursive least squares algorithm.

Reference throughout this specification to features, advantages, or similar language does not imply that all of the features and advantages that may be realized with the subject matter of the present disclosure should be or are in any single embodiment of the subject matter. Rather, language referring to the features and advantages is understood to mean that a specific feature, advantage, or characteristic described in connection with an embodiment is included in at least one embodiment of the subject matter of the present disclosure. Thus, discussion of the features and advantages, and similar language, throughout this specification may, but do not necessarily, refer to the same embodiment.

Furthermore, the described features, advantages, and characteristics of the subject matter of the present disclosure may be combined in any suitable manner in one or more embodiments. One skilled in the relevant art will recognize that the subject matter of the present disclosure may be practiced without one or more of the specific features or advantages of a particular embodiment. In other instances, additional features and advantages may be recognized in certain embodiments that may not be present in all embodiments of the subject matter of the present disclosure.

These features and advantages of the present subject matter of the present disclosure will become more fully apparent from the following description and appended claims, or may be learned by the practice of the subject matter of the present disclosure as set forth hereinafter.

BRIEF DESCRIPTION OF THE DRAWINGS

In order that the advantages of the subject matter of the present disclosure will be readily understood, a more particular description of the subject matter briefly described above will be rendered by reference to specific embodiments that are illustrated in the appended drawings. Understanding that these drawings depict only typical embodiments of the subject matter of the present disclosure and are not therefore to be considered to be limiting of its scope, the subject matter will be described and explained with additional specificity and detail through the use of the accompanying drawings, in which.

DETAILED DESCRIPTION

Figure 1:
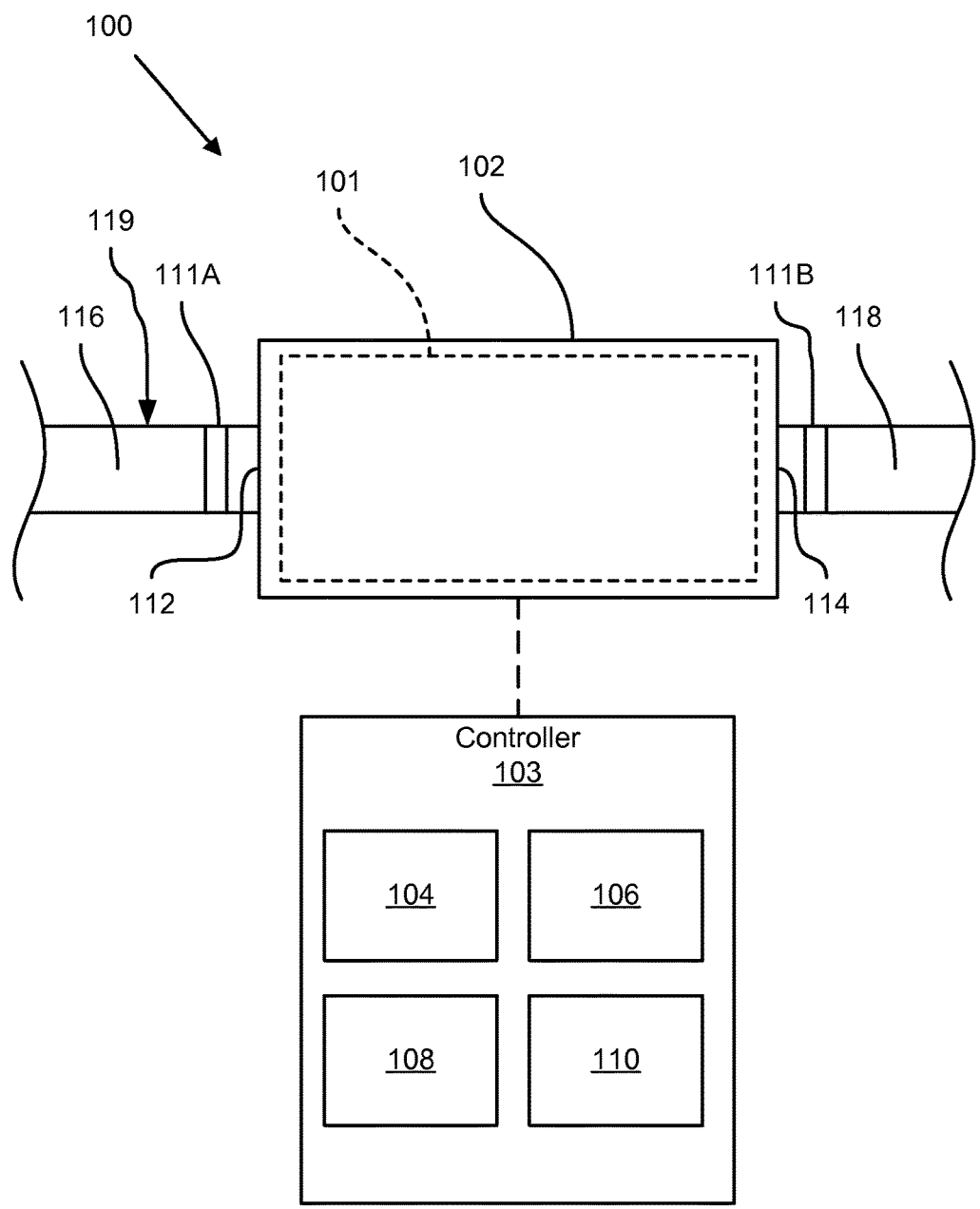
FIG. 1 is a schematic diagram of one embodiment of an apparatus to detect the presence of a catalyst in a catalyst housing.

FIG. 1 depicts a schematic diagram of one embodiment of an apparatus 100 to detect the presence of a catalyst device 101 in a catalyst housing 102. The apparatus 100 includes a controller 103 that includes a temperature module 104, a flow rate module 106, an expected time delay module 108, and a similarity module 110. The temperature module 104, flow rate module, expected time delay module 108, and the similarity module 110 are communicable with each other via electric signal communication. The controller 103 in FIG. 1 is depicted as a single physical unit, but can include two or more physically separated units or components in some embodiments if desired. Generally, the controller 103 receives one or multiple inputs, processes the inputs, and transmits one or multiple outputs. The inputs may include sensed measurements from sensors (e.g., sensor modules 111A, 111B) and various user inputs. The inputs are processed by the controller 103 using various algorithms, stored data, and other inputs to update the stored data and/or generate output values. The generated output values and/or commands are transmitted to other components of the controller and/or to one or more elements of the apparatus 100 or associated engine system to control the apparatus and/or system to achieve desired results.

In the apparatus 100, exhaust gas flows into an inlet 112 of the catalyst housing 102, through the catalyst housing, and out of an outlet 114 of the catalyst housing. The exhaust gas may come from a diesel internal combustion engine, a gasoline internal combustion engine, or any other exhaust producing device. In one embodiment, the catalyst housing 102 is designed to receive and house a catalyst 101. The catalyst 101 can be removable from the catalyst housing 102. Additionally, the catalyst 101 can be replaceable and may be removed and replaced by a user by accessing (e.g., opening) the housing.

As discussed above, exhaust gas flows within and through the catalyst housing 102. Exhaust gas can flow through the catalyst housing 102 when the catalyst 101 is present within the catalyst housing 102, as well as when the catalyst is not present within the catalyst housing 102. In one embodiment, the catalyst housing 102 is connected at the inlet 112 to a first portion 116 of an exhaust gas tube 119 and is connected at the outlet 114 to a second portion 118 of the exhaust gas tube. The first portion 116 of the exhaust gas tube 119 is connected directly or indirectly to a diesel engine at an end opposite the end coupled to the inlet 112 of the catalyst housing 102.

The catalyst device 101 may include any type of catalyst used to interact with exhaust gas flowing through the housing 102. In one embodiment, the catalyst device 101 is a selective catalytic reduction (SCR) catalyst. In another embodiment, the catalyst device 101 is a diesel oxidation catalyst (DOC) used to promote the oxidation of diesel exhaust gasses. In another embodiment, the catalyst device 101 is a DOC and a diesel particulate filter (DPF). In another embodiment, the catalyst device 101 is a DPF. In another embodiment, the catalyst device 101 is a lean NOx catalyst (LNC) designed to reduce nitrogen oxides from diesel exhaust gas. One of skill in the art will recognize other catalysts or catalyst devices that may be placed within the catalyst housing.

In one embodiment, the temperature module 104 detects, calculates, or otherwise determines a temperature of exhaust gas at the inlet 112 of the catalyst housing 102 and a temperature of exhaust gas at the outlet 114 of the catalyst housing 102 using common techniques employed in the art. In one implementation, the temperature module 104 determines the housing inlet and outlet temperatures of the exhaust gas based on respective temperature readings detected by the inlet and outlet sensor modules 111A, 111B. The inlet and outlet sensor modules 111A, 111B may include respective inlet and outlet temperature sensors in temperature sensing communication with exhaust gas flowing into and out of the housing 102. The inlet temperature determined by the temperature module 104 may be different than the outlet temperature determined by the temperature module due to, for example, temperature sensor uncertainty, heat loss to ambient air, and the dynamics added by the heat capacity of both the catalyst 101 and catalyst housing 102.

The inlet and outlet temperatures determined by the temperature module 104 are communicated to the expected time delay module 108.

The flow rate module 106 detects, calculates, or otherwise determines a flow rate of the exhaust gas through the exhaust tube 119 using common techniques employed in the art. Accordingly, the flow rate module 106 detects the flow rate of exhaust gas into and through the catalyst housing 102. The determination of the exhaust flow rate by the flow rate module 106 may be based on the flow rate readings detected by a flow rate sensor located at any of various locations, such as upstream of the inlet of the catalyst housing 102, downstream of the outlet of the catalyst housing, and within the catalyst housing 102. In certain implementations, one or both of the sensor modules 111A, 111B includes a flow rate sensor in flow rate sensing communication with exhaust gas. The flow rate module 106 may also determine the flow rate of exhaust gas through the housing 102 via a virtual sensor as is commonly used in the art. The value of the virtual sensor may be provided by an engine control module in some implementations. In one embodiment, the flow rate module 106 communicates the determined flow rate of the exhaust gas to the similarity module 110.

The expected time delay module 108 estimates an expected time delay between the detected inlet and outlet exhaust gas temperatures for a system with a catalyst present. Generally, the presence or absence of a catalyst from the catalyst housing 102 changes the thermal dynamics within the catalyst housing 102. For example, the presence of a catalyst increases the heat capacity within the housing 102, which results in a time delay between the inlet and outlet exhaust gas temperatures. In certain implementations, the expected time delay can be approximated with a pure time delay, which is the time for a fluctuation in the inlet temperature to be observed by the outlet temperature sensor. Accordingly, the exhaust temperature observed with the outlet temperature sensor can be defined as a delayed inlet exhaust temperature. The time delay as defined above is not affected by temperature sensor uncertainty, which normally is indicated by an offset between reading or sensed values and actual values due to sensor part-to-part variations, because the time delay is independent of an actual-to-sensed temperature comparison.

If a catalyst is not present, then the heat capacity is reduced and the system does not experience a significant time delay between the inlet and outlet exhaust gas temperatures. Generally, if the expected time delay between the inlet and outlet exhaust gas temperatures, as estimated by the time delay module 108, is not found, a missing catalyst fault is set. In one embodiment, the expected time delay module 108 estimates the expected time delay D based on the exhaust gas flow rate determined by the flow rate module 106. In one embodiment, the expected time delay D is calculated or estimated from the function D(k), which is the expected time delay D at the catalyst detection execution time k. In other embodiments, other means or methods recognized by one of skill in the art in view of the present disclosure may be used to estimate an expected time delay between the detected inlet and outlet exhaust gas temperatures.

Figure 2:
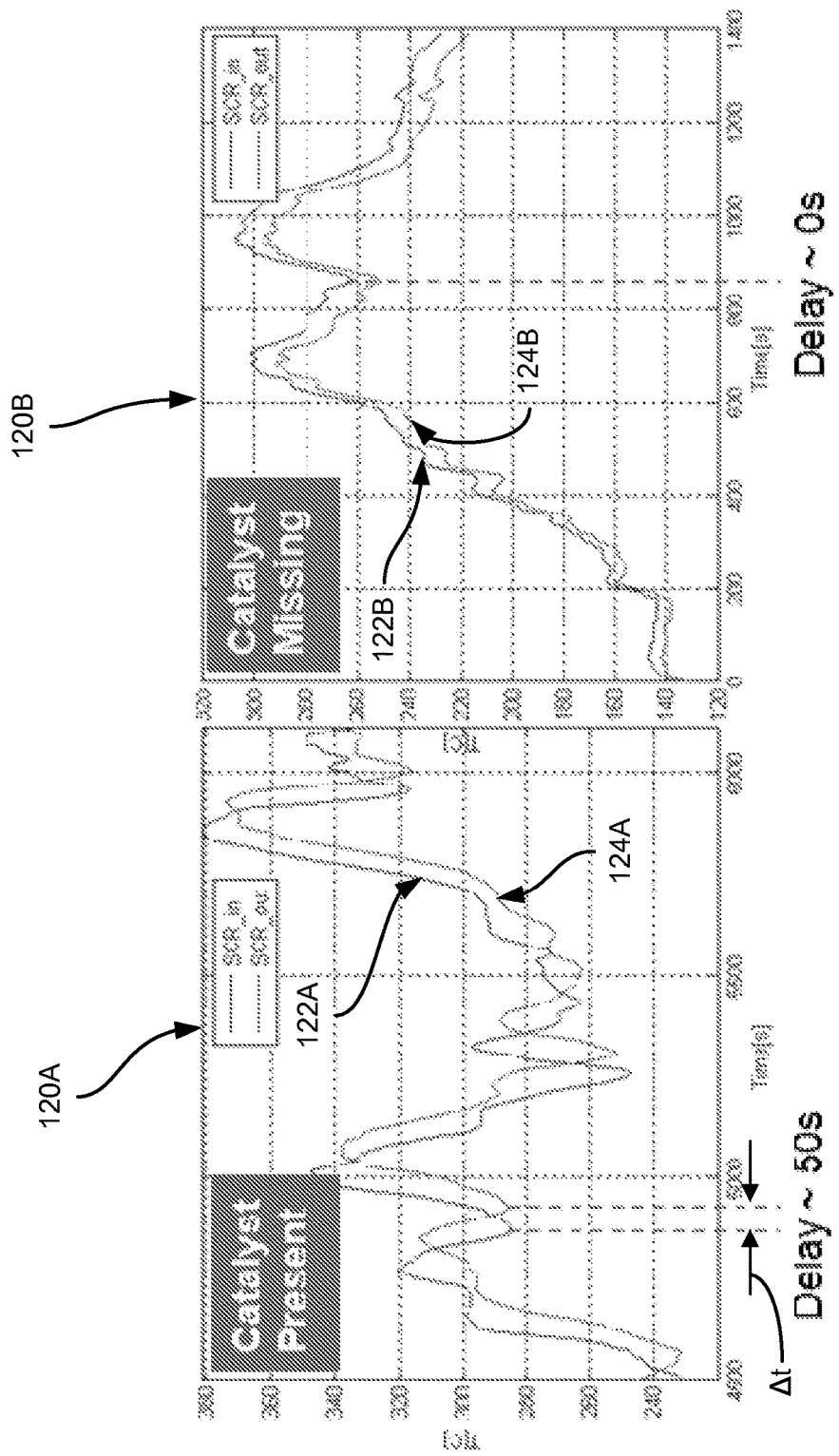
FIG. 2 depicts two graphical representations of a time versus temperature comparison for a catalyst present scenario and a catalyst missing scenario.

FIG. 2 depicts two temperature versus time comparison graphs 120A, 120B for a system with a catalyst present and a system without a catalyst present, respectively. Each comparison graph 120A, 120B displays temperature on a y-axis and time on an x-axis. The catalyst present graph 120A shows an inlet exhaust temperature line 122A representing the detected temperature of exhaust gas entering a catalyst housing and an outlet temperature line 124A representing the detected temperature of exhaust gas exiting the catalyst housing. The catalyst missing graph 120B shows a detected inlet exhaust temperature line 122B and a detected outlet exhaust temperature line 124B. As shown in the catalyst missing graph 120B, when a catalyst is missing from the catalyst housing 102, the detected outlet temperature line 124B and the detected inlet temperature line 122B closely coincide. This corresponds to a small time delay (e.g., approximately zero seconds) or no lag between the detected inlet and outlet exhaust gas temperatures, which indicates the absence of a catalyst. In contrast, as shown in the catalyst present graph 120A, when a catalyst is present in the catalyst housing 102 the detected outlet temperature line 124A lags the detected inlet temperature line 122A by a certain time difference (see, e.g., time difference Δt). The lag corresponds to a larger time delay (e.g., approximately 50 seconds in the illustrated implementation) between the detected inlet and outlet exhaust gas temperatures, which indicates the presence of a catalyst.

In one embodiment, the expected time delay module 108 estimates the expected time delay associated with the delayed inlet exhaust temperature with a Padé approximation of a pure time delay. The transfer function H(s) of a continuous dynamical system composed of a pure time delay is:

$$H(s) = e^{-Ds} \quad (1)$$

where s is the Laplace parameter and D is the desired time delay. The Padé approximation $\tilde{H}(s)$ is a fractional polynomial that approximates the pure delay transfer function. For example, the Padé approximation with numerator of degree zero and denominator of degree one is given by:

$$\tilde{H}(s) = \frac{1}{1 + Ds} \quad (2)$$

This transfer function can be converted to the continuous time domain and then discretized to be implemented efficiently using a discrete time linear filter in a digital computer such as an automotive ECM. Alternatively, the inlet exhaust temperature delayed by D seconds can be calculated by using a data buffer which is designed to contain the last $D/t_s$ samples of the inlet exhaust temperature, where D is a multiple of the sampling time $t_s$. The inlet exhaust temperature delayed by D seconds can be systematically retrieved from this data buffer.

Referring back to FIG. 1, the similarity module 110 determines the absence or presence of a catalyst by comparing the outlet temperature of the exhaust gas with two other signals: the inlet temperature of the exhaust gas and the inlet temperature of the exhaust gas delayed by D seconds. The inlet temperature without time delay represents the expected outlet temperature for a system with a missing catalyst. The inlet temperature with time delay represents the expected outlet temperature for a system with a catalyst present. In one implementation, if the outlet temperature is similar to the artificially delayed inlet temperature, a fault is cleared. In the same implementation, if the outlet temperature of the exhaust gas is similar to the inlet temperature of the exhaust gas, a fault is set. In one embodiment, a set fault indicates the absence of a catalyst or damage to the catalyst within the catalyst housing 102.

In yet another embodiment, the similarity module 110 determines the absence or presence of a catalyst by determining a temperature similarity value based on the detected inlet and outlet exhaust gas temperatures and the estimated expected time delay D. In one embodiment, the temperature similarity value ranges from approximately zero to approximately one. If the similarity value is close to one, the outlet temperature is considered to be similar to the artificially delayed inlet temperature. Accordingly, when the similarity value is close to one, the similarity module 110 reports that a catalyst is present within the catalyst housing 102. If, however, the similarity value is close to zero, the outlet temperature is considered to be similar to the inlet temperature. Accordingly, when the similarity value is close to zero, the similarity module 110 reports that a catalyst is not present within the catalyst housing 102.

More generally, the similarity module 110 determines that a catalyst is present within the catalyst housing 102 if the determined temperature similarity value is above a first threshold, which can be a number close to a value of one in certain implementations. The similarity module 110 determines that a catalyst is not present if the determined temperature similarity value is below a second threshold, which can be a number close to a value of zero. In certain implementations, the first and second thresholds are the same or similar.

The outlet temperature signal resembles the inlet temperature signal when a catalyst is missing and resembles the inlet temperature delayed by D seconds when the catalyst is present. In one embodiment, the temperature similarity is defined as the parameter a that solves the following optimization problem:

$$\hat{a} = \operatorname*{argmin}_{a} \sum_{k} (T_o(k) - (aT_i(k-D) + (1-a)T_i(k)))^2 \quad (3)$$

where $\hat{a}$ is the estimated similarity value, $T_o$ is the outlet temperature, $T_i$ is the inlet temperature, D is the expected delay, k is a discrete sample time, and the summation is over a predefined number of samples preceding the current time. If $\hat{a}$ is close to 1, $T_o(k)$ is closer to the $T_i(k-D)$ in the least squares sense. Conversely, if $\hat{a}$ is close to 0, $T_o(k)$ is closer to the $T_i(k)$. The apparatus 100 solves the optimization problem (e.g., Equation 3), which is an unconstrained least square problem, before a diagnosis regarding the presence or absence of a catalyst is made.

In another embodiment, the temperature similarity is defined as the parameter a that solves the following optimization problem:

$$\hat{a} = \operatorname*{argmin}_{a,b,g} \sum_{k} (T_o(k) - a(gT_i(k-D) + h) - (1-a)(gT_i(k) + h))^2 \quad (4)$$

where $\hat{a}$ is an optimal or estimated similarity value, g is a inlet temperature sensor gain error correction, h is an inlet temperature sensor offset error correction, $T_o$ is the outlet temperature, $T_i$ is the inlet temperature, D is the expected delay, k is a discrete sample time, and the summation is over a predefined number of samples preceding the current time. The parameters g and h model the differences in gain and offset of the inlet sensor relative to the outlet sensor. One reason for estimating the sensor gain g and the sensor offset h is to make the similarity calculation less sensitive to part-to-part sensor variations and ambient heat loss. In view of the present disclosure, one skilled in the relevant art may recognize alternative objective functions to calculate a similarity measure such as a.

In one embodiment, the optimization problem is solved as presented in Equation 3 and Equation 4. In another embodiment, the optimization problem is modified to be solved recursively using a recursive least squares algorithm which is implemented in a parameter estimate module or function (see FIG. 3). In one embodiment, a decision of whether or not a catalyst is present is made by the similarity module 110 according to the following algorithm:

$$\text{Decision} \begin{cases} \hat{a} > Thd \Rightarrow \text{Error} = 0 \\ \hat{a} \leq Thd \Rightarrow \text{Error} = 1 \end{cases} \quad (5)$$

where Thd is a decision threshold.

Figure 3:
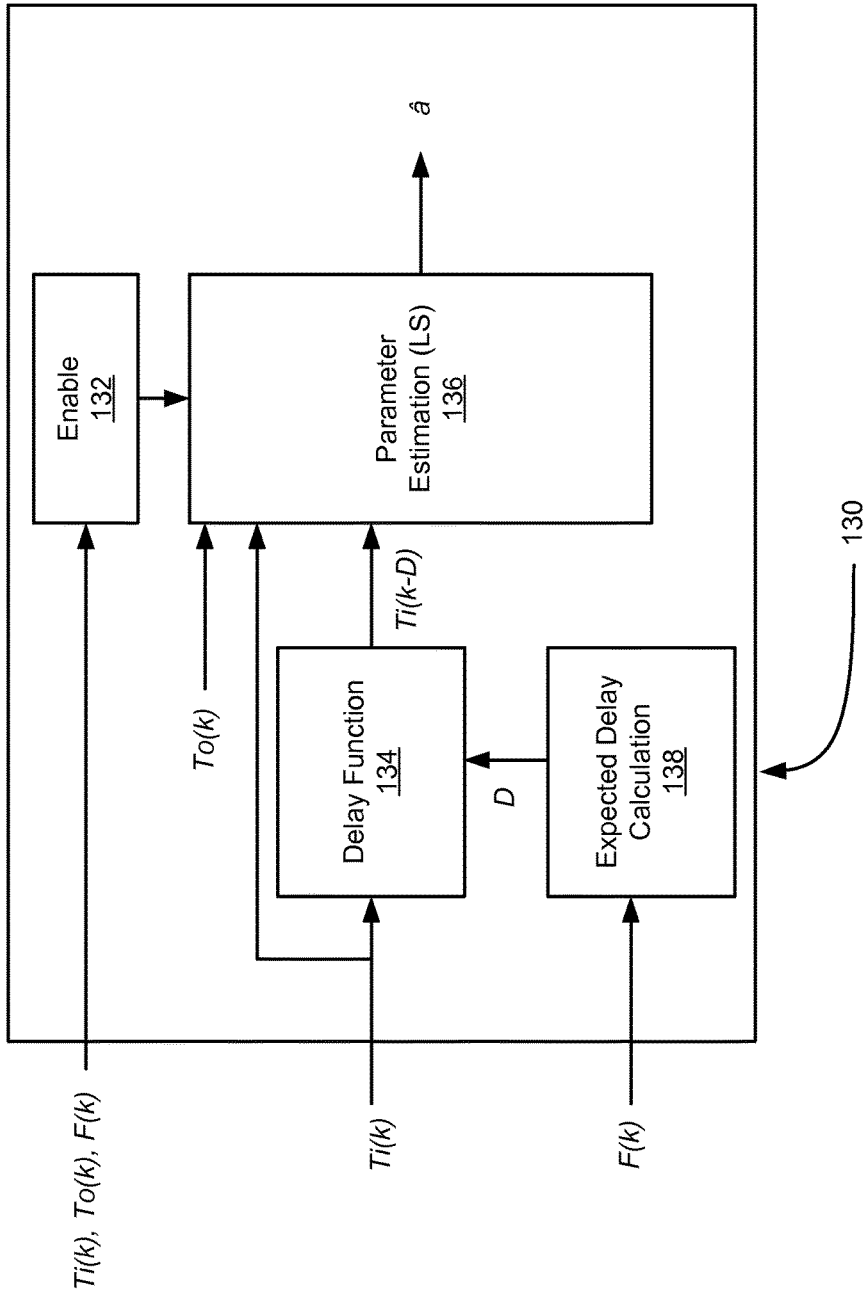
FIG. 3 depicts a flow chart diagram of one embodiment of an apparatus to detect the presence of a catalyst.

FIG. 3 depicts a schematic flow diagram of one embodiment of a control system 130 of the apparatus 100. In one embodiment, the control system 130 receives a flow rate of exhaust gas F(k) from the flow rate module 106, and an inlet exhaust temperature $T_i(k)$ and outlet exhaust temperature $T_o(k)$ from the temperature module 104. The control system 130 includes an enablement function 132 that determines whether operating conditions are conducive to determining a similarity parameter based on the exhaust flow rate F(k), exhaust inlet temperature $T_i(k)$, and exhaust outlet temperature $T_o$ (k). In certain implementations, the enablement function 132 indicates conditions are conducive to determining a similarity parameter if one or more of the following conditions are met: (i) the exhaust flow falls within a specified range; (ii) the inlet and outlet temperatures fall within respective specified ranges; and (iii) an inlet temperature change rate is within a predetermined range. Regarding the inlet temperature change rate threshold, slow thermal changes may make the delayed temperature or similarity parameter estimation inaccurate. For example, during thermal equilibrium, no time delay can be observed. Conversely, extremely high thermal change rates changes may lead to a poor delayed temperature or similarity parameter estimation when a low order Padé approximation is used.

Further, the control system 130 includes a delay function 134 that has two inputs: the inlet exhaust temperature and the expected delay D. The output of the delay function is the inlet temperature delayed by D seconds (i.e., $T_i(k-D)$). The expected time delay D at any given time is calculated by the delay estimator 138. The delay D depends on the exhaust gas flow as it affects the heat transfer between the exhaust gas and the catalyst. In this embodiment, the delay D is calculated as an empirical function of the exhaust flow F(k). The higher the exhaust flow, the shorter the time delay. One skilled in the relevant art will recognize alternative approaches to estimate the delay D based on other parameters such like exhaust gas pressure, exhaust gas temperature, turbo gas flow, and engine speed in view of the present application.

The inlet exhaust temperature $T_i(k)$, outlet exhaust temperature $T_o$ (k), and delayed inlet exhaust temperature $T_i(k-D)$ are then applied to Equation 3 or Equation 4 at the parameter estimation function 136. The parameter estimation function 136 optimizes Equation 3 or Equation 4 as described above to produce a similarity value a. The similarity value, a, is then applied to Equation 3 to determine the presence of a catalyst within the catalyst housing 102.

Figure 4:
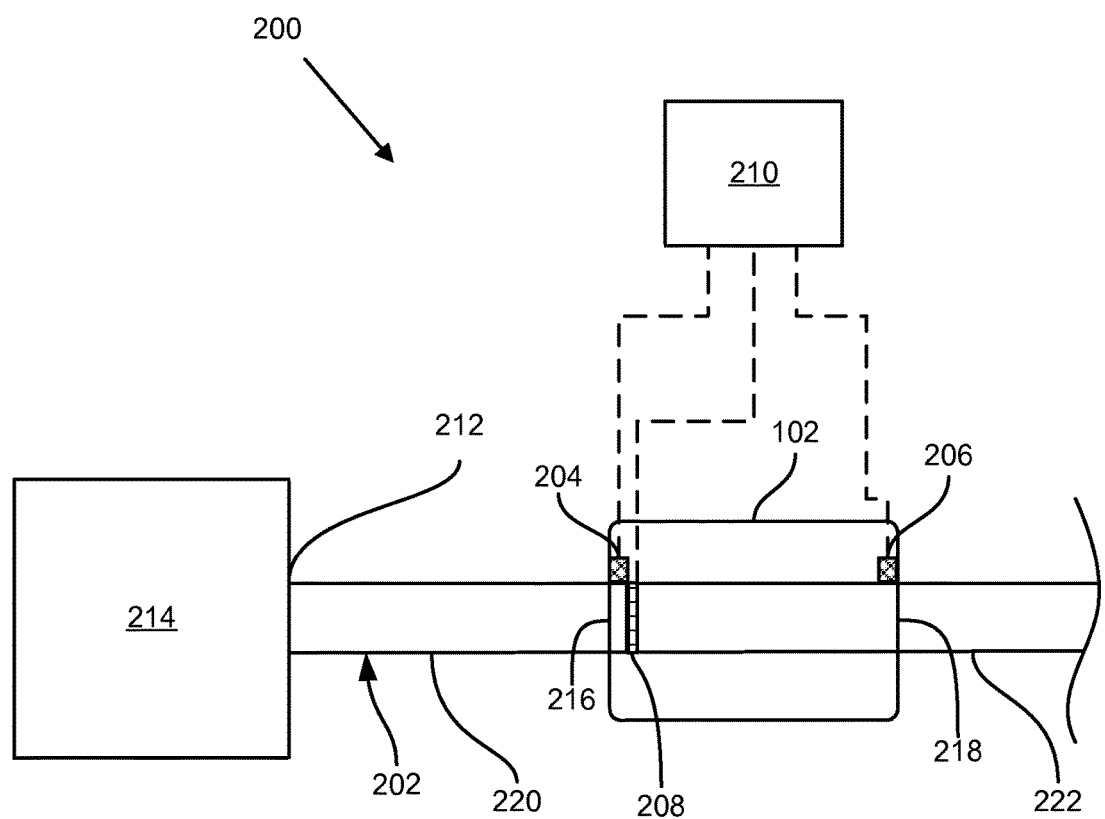
FIG. 4 is a schematic diagram of one embodiment of a system to detect the presence of a catalyst.

FIG. 4 depicts a schematic diagram of one embodiment of a system 200 to detect the presence of a catalyst. The system 200 includes an exhaust gas tube 202, a first temperature sensing device 204, a second temperature sensing device 206, a flow rate measurement device 208, and a processing device 210.

In one embodiment, the exhaust gas tube 202 is coupled to a diesel engine 214 at a first end 212. Exhaust gas from the diesel engine 214 is flowable through the exhaust gas tube 202. The exhaust gas from the diesel engine 214 flows into a catalyst housing entrance 216 and out of a catalyst housing exit 218.

The first temperature sensing device 204 is coupled to an upstream portion 220 of the exhaust gas tube 202. The temperature of the exhaust gas is measured at a location of the first temperature sensing device 204 and is defined as the first temperature of exhaust gas. The second temperature sensing device 206 is coupled to a downstream portion 222 of the exhaust gas tube 202. The second temperature sensing device 206 measures a second temperature of the exhaust gas at a position of the second temperature sensing device 206. In one embodiment, the first and second temperature sensing devices 204, 206 output a first and second temperature of exhaust gas, respectively, to the processing device 210.

The flow rate measurement device 208 of the system 200 measures a flow rate of the exhaust gas in the exhaust gas tube 202. In another embodiment, the flow rate measurement device 208 measures a flow rate of the exhaust gas in the catalyst housing 102. As shown, the flow rate measurement device 208 is positioned between the first and second temperature sensing devices 204, 206. In another embodiment, the flow rate measurement device 208 is positioned outside of the first and second temperature sensing devices 204, 206. In one embodiment, the flow rate measurement device 208 outputs a flow rate reading to the processing device 210. In another embodiment, the flow rate is estimated using, for example, atmospheric conditions, engine parameters and aftertreatment parameters.

The processing device 210 estimates an expected time delay between the measured inlet and outlet exhaust gas temperatures for a catalyst housing 102 with catalyst present. In one embodiment, the expected time delay is calculated using the flow rate measured by the flow rate measurement device 208. The processing device 210 also determines the presence of a catalyst. In one embodiment, the processing device 210 determines the presence of a catalyst by comparing the measured outlet temperature to the measured inlet temperature, and by comparing the measured outlet temperature to the measured inlet temperature delayed by D seconds. In one embodiment, the estimated expected delay D is calculated as a function of the exhaust flow rate. If the measured outlet temperature is similar to the measured inlet temperature, the processing device 210 outputs an error message. If the measured outlet temperature and the delayed inlet temperature are similar, the processing device 210 outputs a clear message. Accordingly, the processing device 210 uses both a comparison of the measured outlet exhaust temperature to the measured inlet exhaust temperature and a comparison of the measured outlet exhaust temperature to an estimated delayed inlet exhaust temperature to determine if a catalyst is present within the catalyst housing 102.

Figure 5:
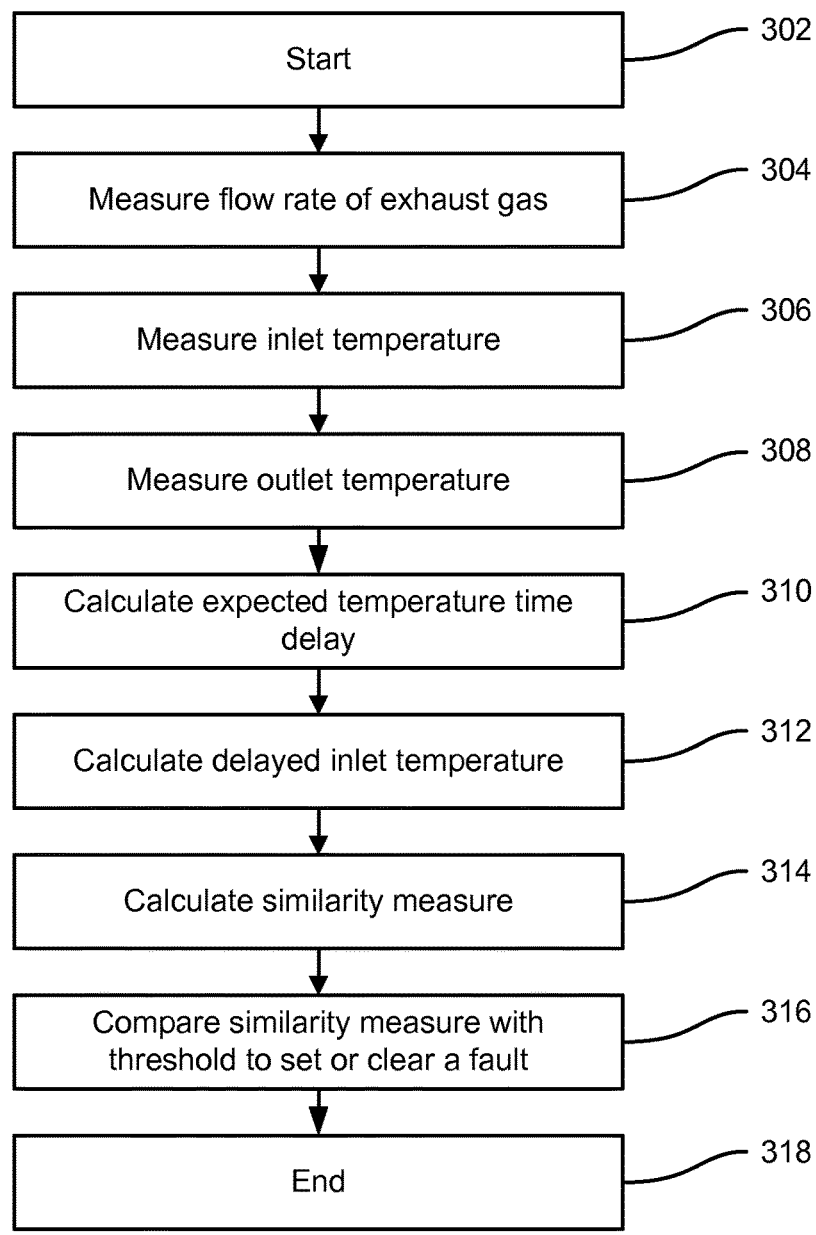
FIG. 5 is a schematic block diagram illustrating one embodiment of a method for detecting the presence of a catalyst.

FIG. 5 depicts a schematic block diagram illustrating one embodiment of a method 300 for detecting the presence of a catalyst. The method 300 starts at 302 and a flow rate of exhaust gas within an exhaust gas tube is measured at 304. The flow rate may be measured from within the exhaust gas tube or from within a catalyst housing. An inlet temperature of the exhaust gas is measured at 306 at an inlet of the exhaust gas tube. An outlet temperature of the exhaust gas is measured at 308 at an outlet of the exhaust gas tube. An expected temperature time delay is calculated at 310 as a function of the measured flow rate.

A delayed inlet temperature is also calculated at 312 based on the calculated expected temperature time delay and the inlet temperature. A similarity measure is calculated at 314 based on the outlet temperature, the inlet temperature and the inlet temperature delayed by D seconds. In one embodiment, the similarity measure is defined as the solution of an optimization problem, such as those represented in Equation 3 and Equation 4. The similarity measure is compared at 316 to the decision threshold to set or clear the fault. The method 300 then ends at 318.

Figure 6:
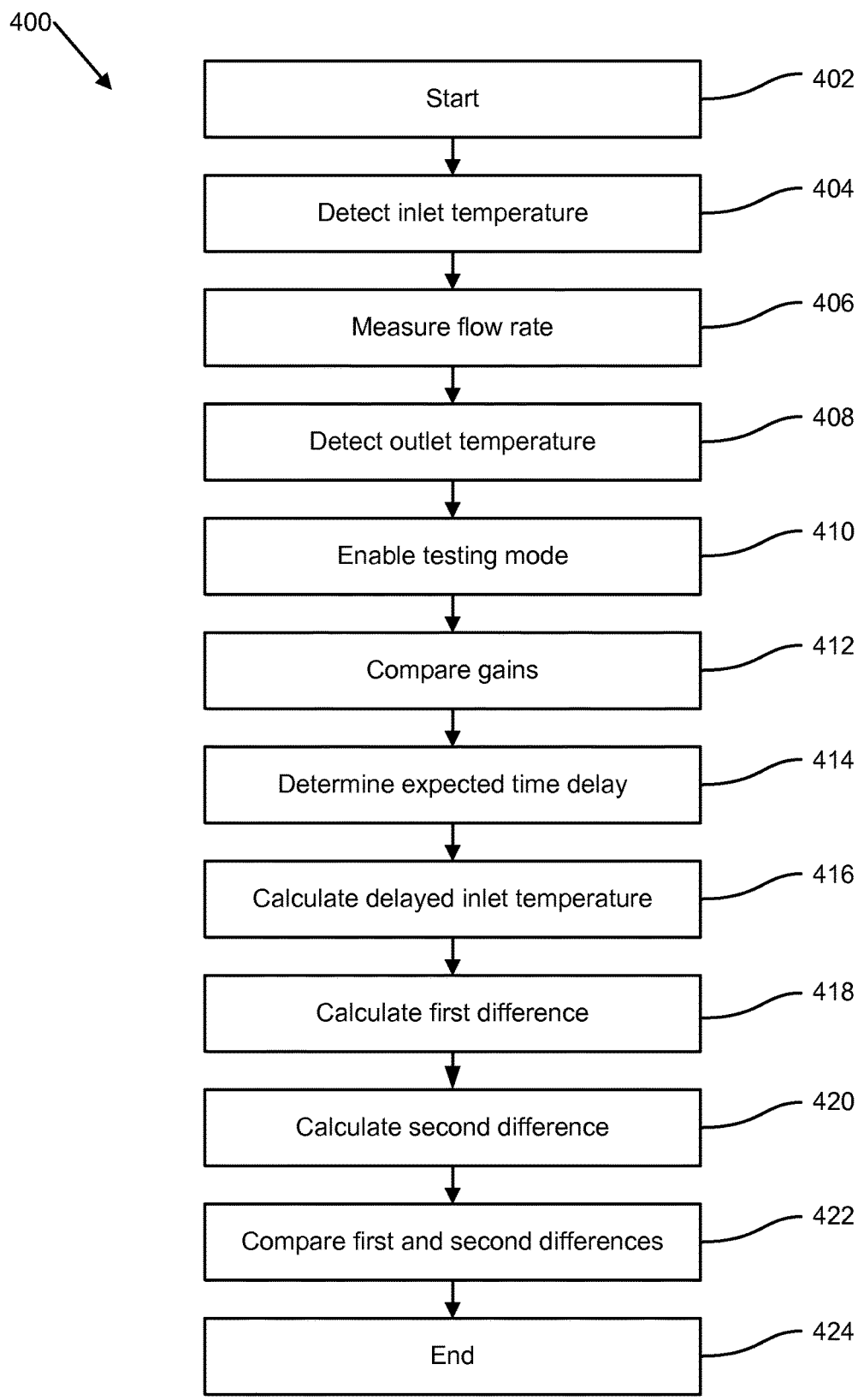
FIG. 6 is a schematic block diagram illustrating another embodiment of a method for detecting the presence of a catalyst.

FIG. 6 depicts a schematic block diagram illustrating another embodiment of a method 400 for detecting the presence of a catalyst. The method 400 starts at 402 and an inlet temperature of exhaust gas within an exhaust gas tube is detected at 404 with a first temperature detection device. The flow rate of the exhaust gas within the exhaust gas tube is measured at 406. Also, an outlet temperature of the exhaust gas within the exhaust gas tube is detected at 408 using a second temperature detection device. Further, a testing module is enabled at 410.

The gain of the first temperature detection device and the gain of the second temperature detection device are compared at 412 to calibrate the first temperature detection device and the second temperature detection device. In one embodiment, comparing the sensor gain from the first temperature detection device and the second temperature detection device may allow a user to implement an automatic gain adjustment to compensate for part-to-part variations and ambient temperature.

An expected time delay between the measured inlet and outlet temperatures is determined at 414. A delayed inlet temperature is calculated at 416. A first difference between the measured outlet temperature and the inlet temperature is calculated at 418 and a second difference between the measured outlet temperature and the delayed inlet temperature is also calculated at 420. The first difference signal and second difference signal are compared at 422 over a period of time. If the first difference signal is smaller than the second difference signal by a specified magnitude or in some other specified sense or characteristic, an error message is output. The specified difference between the first and second difference signals can be determined using, for example, a mathematical norm. The method 400 then ends at 424.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Reference throughout this specification to "one embodiment," "an embodiment," or similar language means that a particular feature, structure, or characteristic described in connection with the embodiment is included in at least one embodiment of the subject matter of the present disclosure. Thus, appearances of the phrases "in one embodiment," "in an embodiment," and similar language throughout this specification may, but do not necessarily, all refer to the same embodiment.

As discussed above, the described features, structures, or characteristics of the subject matter of the present disclosure may be combined in any suitable manner in one or more embodiments. In the above description, numerous specific details are provided, such as examples of modules, catalysts, etc., to provide a thorough understanding of embodiments of the subject matter of the present disclosure. One skilled in the relevant art will recognize, however, that the subject matter of the present disclosure may be practiced without one or more of the specific details, or with other methods, components, materials, and so forth. In other instances, well-known structures, materials, or operations are not shown or described in detail to avoid obscuring aspects of the subject matter of the present disclosure.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter of the present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for detecting the presence of a catalyst, the method comprising:
   measuring a flow rate of exhaust gas within an exhaust gas tube;
   measuring an inlet temperature of the exhaust gas at an inlet of the exhaust gas tube;
   calculating an expected temperature time delay as a function of the measured flow rate;
   measuring an outlet temperature of the exhaust gas at an outlet of the exhaust gas tube;
   calculating a delayed inlet temperature based on the calculated expected temperature time delay and the inlet temperature;
   calculating a first difference between the measured outlet temperature and the inlet temperature and a second difference between the measured outlet temperature and the delayed inlet temperature;
   determining a catalyst is not present if the first difference is the same or smaller than the second difference, and a catalyst is present if the second difference is smaller than the first difference.

2. The method of claim 1, further comprising:
   outputting an error message if the first difference is the same or smaller than the second difference, the error message indicating that the catalyst is not present.

3. The method of claim 1, further comprising comparing a gain of a first temperature detection device that measures the inlet temperature of the exhaust gas at the inlet of the exhaust gas tube and a gain of a second temperature detection device that measures the outlet temperature of the exhaust gas at the out of the exhaust gas tube to calibrate the first temperature detection device and the second temperature detection device.

4. The method of claim 1, wherein calculating the expected temperature time delay as a function of the measured flow rate is performed via a Padé approximation of a pure time delay transfer function.

5. The method of claim 1, further comprising:
   determining if a flow rate of the exhaust gas falls within a first predetermined range; and
   if the flow rate of the exhaust gas falls within the first predetermined range, calculating the expected temperature time delay.

6. The method of claim 1, further comprising:
   determining if the inlet temperature of the exhaust gas falls within a second predetermined range;
   determining if the outlet temperature of the exhaust gas falls within a third predetermined range; and
   calculating the delayed inlet temperature if the inlet temperature falls within the second predetermined range and the outlet temperature falls within the third predetermined range.

7. The method of claim 1, further comprising:
   determining a change rate of the inlet temperature of the exhaust gas;
   determining if the change rate of the inlet temperature falls within a fourth predetermined range; and
   calculating the delayed inlet temperature if the change rate falls within the fourth predetermined range.

8. A method for detecting the presence of a catalyst in an exhaust gas tube, the method comprising:
   measuring a flow rate of exhaust gas within an exhaust gas tube;
   measuring an inlet temperature of the exhaust gas at an inlet of the exhaust gas tube;
   calculating an expected temperature time delay as a function of the measured flow rate;
   measuring an outlet temperature of the exhaust gas at an outlet of the exhaust gas tube;

calculating a delayed inlet temperature based on the calculated expected temperature time delay and the inlet temperature;

calculating a similarity value by comparing the outlet temperature of the exhaust gas to: (1) the inlet temperature of the exhaust gas; and (2) the delayed inlet temperature;

comparing the similarity value to a predetermined threshold; and determining if a catalyst is present or not present based on the comparison between the similarity value and the predetermined threshold.

9. The method of claim 8, further comprising, if it is determined that the catalyst is not present, reporting that the catalyst is not present.

10. The method of claim 8, wherein calculating the similarity value comprises solving an optimization problem.

11. The method of claim 8, wherein calculating the similarity value comprises using a recursive least squares algorithm.

12. The method of claim 8, wherein calculating the expected temperature time delay as a function of the measured flow rate is performed via a Padé approximation of a pure time delay transfer function.

13. The method of claim 10, wherein the optimization problem includes $$\hat{a} = \operatorname*{argmin}_{a} \sum_{k} (T_o(k) - (aT_i(k-D) + (1-a)T_i(k)))^2,$$

and wherein â is the estimated similarity value, $T_o$ is the outlet temperature, $T_i$ is the inlet temperature, D is the expected delay, k is a discrete sample time, and the summation is over a predefined number of samples preceding the current time.

14. The method of claim 10, wherein the optimization problem includes $$\hat{a} = \operatorname*{argmin}_{a,b,g} \sum_{k} (T_o(k) - a(gT_i(k-D) + h) - (1-a)(gT_i(k) + h))^2,$$

and wherein â is an optimal or estimated similarity value, g is an inlet temperature sensor gain error correction, h is an inlet temperature sensor offset error correction, $T_o$ is the outlet temperature, $T_i$ is the inlet temperature, D is the expected delay, k is a discrete sample time, and the summation is over a predefined number of samples preceding the current time.

15. The method of claim 8, wherein comparing the similarity value to the predetermined threshold includes determining if the similarity value is above or below the predetermined threshold, and wherein the similarity value is above the predetermined threshold if the outlet temperature of the exhaust gas is similar to the inlet temperature of the exhaust gas, and wherein the similarity value is below the predetermined threshold if the outlet temperature of the exhaust gas is similar to the delayed inlet temperature.

16. The method of claim 15, wherein the catalyst is not present if the outlet temperature of the exhaust gas is similar to the inlet temperature, and the catalyst is present if the outlet temperature of the exhaust gas is similar to the delayed inlet temperature.

17. The method of claim 8, further comprising:
measuring a plurality of time delays between measuring the inlet temperature of the exhaust gas and measuring the outlet temperature of the exhaust gas,
wherein the expected temperature time delay is calculated based on the plurality of measured time delays.

18. The method of claim 8, further comprising:
determining if a flow rate of the exhaust gas falls within a first predetermined range; and
if the flow rate of the exhaust gas falls within the first predetermined range, calculating the expected temperature time delay.

19. The method of claim 8, further comprising;
determining if the inlet temperature of the exhaust gas falls within a second predetermined range;
determining if the outlet temperature of the exhaust gas falls within a third predetermined range; and
calculating the delayed inlet temperature if the inlet temperature falls within the second predetermined range and the outlet temperature falls within the third predetermined range.

20. The method of claim 8, further comprising;
determining a change rate of the inlet temperature of the exhaust gas;
determining if the change rate of the inlet temperature falls within a fourth predetermined range; and
calculating the delayed inlet temperature if the change rate falls within the fourth predetermined range.

* * * * *